United States Patent [19]

Sherman et al.

[11] Patent Number: 5,074,866
[45] Date of Patent: Dec. 24, 1991

[54] TRANSLATION/ROTATION DEVICE FOR EXTERNAL BONE FIXATION SYSTEM

[75] Inventors: Michael C. Sherman, Memphis; Robert Wigginton, Collierville, both of Tenn.; Dror Paley, Baltimore, Md.

[73] Assignee: Smith & Nephew Richards Inc., Memphis, Tenn.

[21] Appl. No.: 598,046

[22] Filed: Oct. 16, 1990

[51] Int. Cl.$^5$ .............................................. A61F 5/04
[52] U.S. Cl. ....................................... 606/56; 606/54; 128/69
[58] Field of Search .......................... 128/69, 68, 80 R; 606/53-54, 56-59

[56] References Cited

U.S. PATENT DOCUMENTS

| 3,976,061 | 8/1976 | Volkov et al. | 606/56 |
|---|---|---|---|
| 3,977,397 | 8/1976 | Kalnberz et al. | 606/57 |
| 4,033,340 | 7/1977 | Kalnberz | 128/92 A |
| 4,365,624 | 12/1982 | Jaquet | 606/56 |
| 4,615,338 | 10/1986 | Ilizarov et al. | 128/92 A |
| 4,620,533 | 11/1986 | Mears | 128/92 Z |

FOREIGN PATENT DOCUMENTS

| 98471 | 6/1952 | U.S.S.R. | |
| 367858 | 6/1973 | U.S.S.R. | |
| 829105 | 5/1981 | U.S.S.R. | 606/57 |
| 848011 | 7/1981 | U.S.S.R. | |
| 865284 | 9/1981 | U.S.S.R. | |
| 986404 | 1/1983 | U.S.S.R. | |
| 1066579 | 1/1984 | U.S.S.R. | 606/56 |
| 1074512 | 2/1984 | U.S.S.R. | 606/57 |
| 1076108 | 2/1984 | U.S.S.R. | 606/58 |
| 1149959 | 4/1985 | U.S.S.R. | 606/53 |

OTHER PUBLICATIONS

"Stretching: The Body's Power to Grow", Parade Magazine, Oct. 8, 1989, pp. 4 and 5.

Primary Examiner—Richard J. Apley
Assistant Examiner—Linda C. M. Dvorak
Attorney, Agent, or Firm—Pravel, Gambrell, Hewitt, Kimball & Krieger

[57] ABSTRACT

Apparatus for the fixation of bone fractures and the correction of congenital deformities uses an improved adjustment device that allows selective rotation or lateral translation of one external fixation ring with respect to other external fixation rings. The adjustment device attaches to a pair of first and second tie rod sections and shifts the first tie rod section with respect to the second tie rod section during adjustment. The adjustment device has a lateral slot that defines the path of movement for one of the translating tie rod sections. A travelling block connected to the moving tie rod section tracks the slot during use.

10 Claims, 5 Drawing Sheets

TRANSLATION/ROTATION DEVICE FOR EXTERNAL BONE FIXATION SYSTEM

BACKGROUND OF THE INVENTION

1. Field of the Invention

The present invention relates to the repair of bone fractures and the correction of bone defects using external fixation frames wherein an adjustment of one frame part with respect to another through translation or rotation is swiftly accomplished using a fine adjustment translator that can be interfaced with the external fixation frame parts.

2. General Background

The repair of traumatized bone can be accomplished by the use of an external fixator device which includes a number of curved rings or curved half rings that are attached and spaced apart but structurally connected using a plurality of tie rods. These tie rods are simply inserted through one of several holes formed in each of the selected half rings or rings at a desired circumferential position and affixed thereto by bolting.

Several rings and several tie rods can be used by the surgeon in order to create an overall frame about the patient's arm or leg. Transversely extending pins or wires attach to these rings and then extend transversely from the rings into the bones, so that the frame and transverse pins support and/or load the bone tissue in a desired manner. This external fixation system is generally referred to in the art as the "Ilizarov technique".

The "Ilizarov" technique can be used for the purpose of external fixation of heavily damaged or heavily traumatized bone. The "Ilizarov" technique can also be used for lengthening various congenital and acquired shortenings and other defects of skeletal segments wherein the rings and tie rods form part of a compression-distraction apparatus.

The "Ilizarov" technique is described generally in the Oct. 8, 1989 issue of Parade Magazine in an article entitled "Stretching The Body's Power To Grow", and in U.S. Pat. No. 4,615,338, issued to Gavril A. Ilizarov et al. The '338 patent, entitled "Automatic Compression-Distraction Apparatus", is directed to an improved compression distraction apparatus. The '338 Ilizarov patent references earlier prior art publications of the same inventor, including USSR Inventor Certificate No. 848,011,cl.A 61 B 17/18, also published in the Bulletin of Inventions No. 27,1981. A second prior art disclosure relating to a drive of a compression distraction apparatus appears in USSR Inventor Certificate No. 865,284,cl.A 61 B 17/18, published in the Bulletin of Inventions No. 35,1981. These prior Ilizarov publications all relate generally to the Ilizarov external fixation system which uses metal rings, threaded rods, threaded fasteners, and other metallic components in the fixation of fractures and the correction of congenital bone deformities.

During the course of treatment of patients undergoing the "Ilizarov" technique, it is at times necessary to translate or rotate one segment of the "Ilizarov" apparatus with respect to the other. Previously, this has been accomplished with standard "Ilizarov" components arranged in such a manner to permit the necessary translation or rotation. A problem with this approach of achieving translation or rotation is that it is exceptionally time consuming for the surgeon to assemble the appropriate construct on the "Ilizarov" frame. In addition, depending upon the unique demands of the particular patient, these constructs can be rather complex and for the new "Ilizarov" surgeon extremely difficult to visualize and assemble.

The Mears Pat. No. 4,620,533 relates to an apparatus for externally fixing bone fractures with clamps having universal ball joints to pins and a rigid bar. Other patents include the Kalnberz Pat. No. 4,033,340 entitled "Surgical Compression Distraction Instrumentation" and 3,977,397 entitled "Surgical Compression Distraction Instrumentation". The '340 patent deals with translation or rotation of an "Ilizarov " type external fixator. In the Kalnberz '340 patent there is provided attachment of an exterior ring to the circular fixator and manipulation of the circular fixator with respect to that external ring is provided. This apparatus thus attempts to provide rotation only. In the Kalnberz '340 patent the surgical instrument is adapted to adjust the position of bone fragments of a limb. It has an outer ring with longitudinal connecting members and a smaller ring carrying clamps for needles fixed within a larger ring. A system of threaded studs enables the inner ring to move in any direction and turn within the outer ring. The inner ring can also be positioned in a plane turned by an angle with respect to the plane of the outer ring.

In the Kalnberz Pat. No. 3,977,397, an instrument for treating injuries and diseases of bones and joints incorporates rings with needles passed through bone fragments. Adjacent rings are interconnected by longitudinal permanently sprung members, namely helical springs and/or rods connected with the rings by means of nuts. To stabilize the structure, strengthening rings composed of separate arches and carrying locking means for additional needles may be inserted into the instrument. The '397 patent discusses an early Ilizarov inventor certificate number 98,471 granted June 9, 1952. Another inventor certificate, USSR inventor certificate number 367858 is discussed in the '340 Kalnberz patent naming inventors Sinilo, Sarancha, and Nadein. The instrument referred to in that inventor certificate comprises a slotted support arch, a distal arch, and a split ring as well as coupling screws, needles and fastening members, the ring being connected with the support arch by means of threaded link studs arranged radially and tangentially with resect to the ring.

SUMMARY OF THE INVENTION

The present invention provides an improved translation/rotation device for use with Ilizarov external fixation systems. The present invention provides a device which is a preassembled construct to achieve translation or rotation, which the surgeon can swiftly insert into an existing "Ilizarov" type external fixation frame. Because the device is whole in nature, it requires no assembly by the Ilizarov surgeon, permitting quick conversion of an existing frame to translation or rotation as desired. The present invention provides an apparatus which is preassembled and adaptable to any size ring. The surgeon need only remove a standard and existing component in the frame and insert the apparatus of the present invention in its place as will be explained more fully hereinafter.

The present invention thus provides an improved bone fixator apparatus for the fixation of fractures and the correction of congenital bone deformities that includes a plurality of ring like structures, each having inner and outer curved surfaces, and spaced parallel flat and upper lower surfaces. A plurality of openings is spaced along each of the ring like structures, positioned between the inner and outer annular curved surfaces and extending between the upper and lower surfaces. A plurality of tie rod assemblies includes rod members extending during use between the ring like structures, connecting adjacent ring like structures together to define a frame. Fasteners are provided for securing each ring like structure to one or more of the tie rods for maintaining spacing between the ring like structures during use. A translation/rotation device interfaces one or more of the tie rods for moving a first ring like structure with respect to a second ring like structure in either of a rotational or translational manner so that one ring can be rotated with respect to the other or move laterally (translated) with respect to the other as selected by the surgeon.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
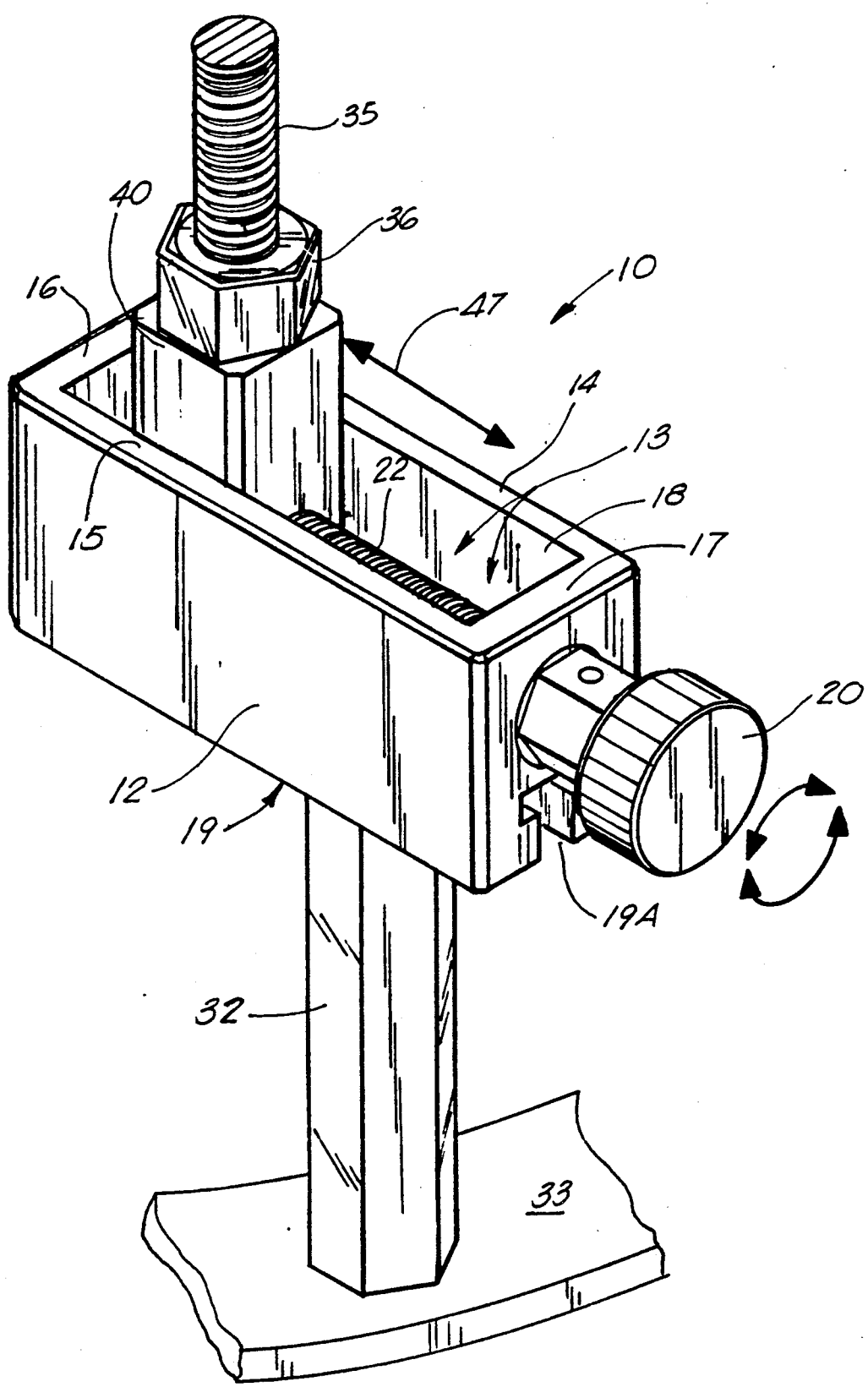
FIG. 1 is a perspective view of the preferred embodiment of the apparatus of the present invention.
Figure 2:
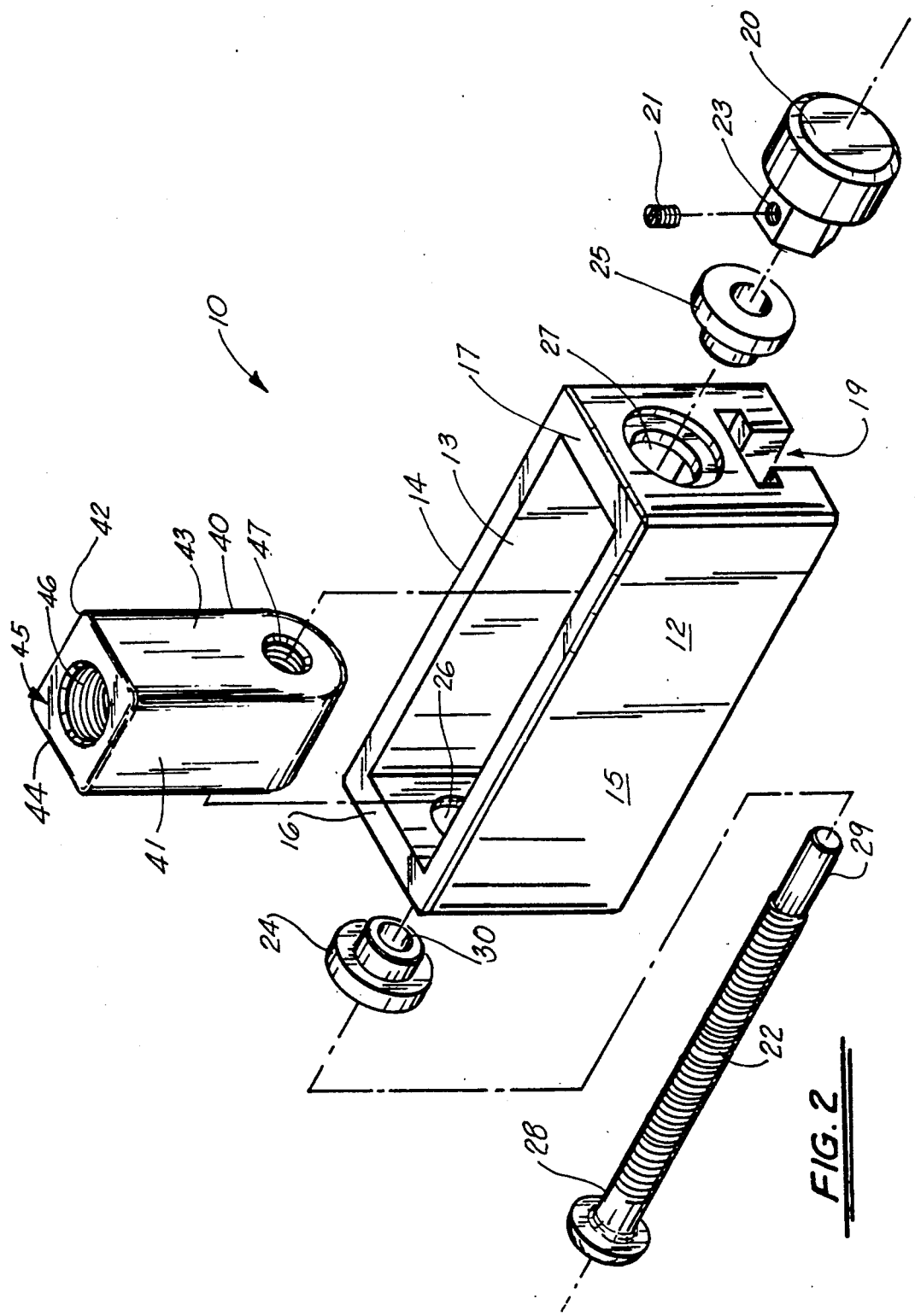
FIG. 2 is an exploded perspective view of the preferred embodiment of the apparatus of the present invention.
Figure 3:
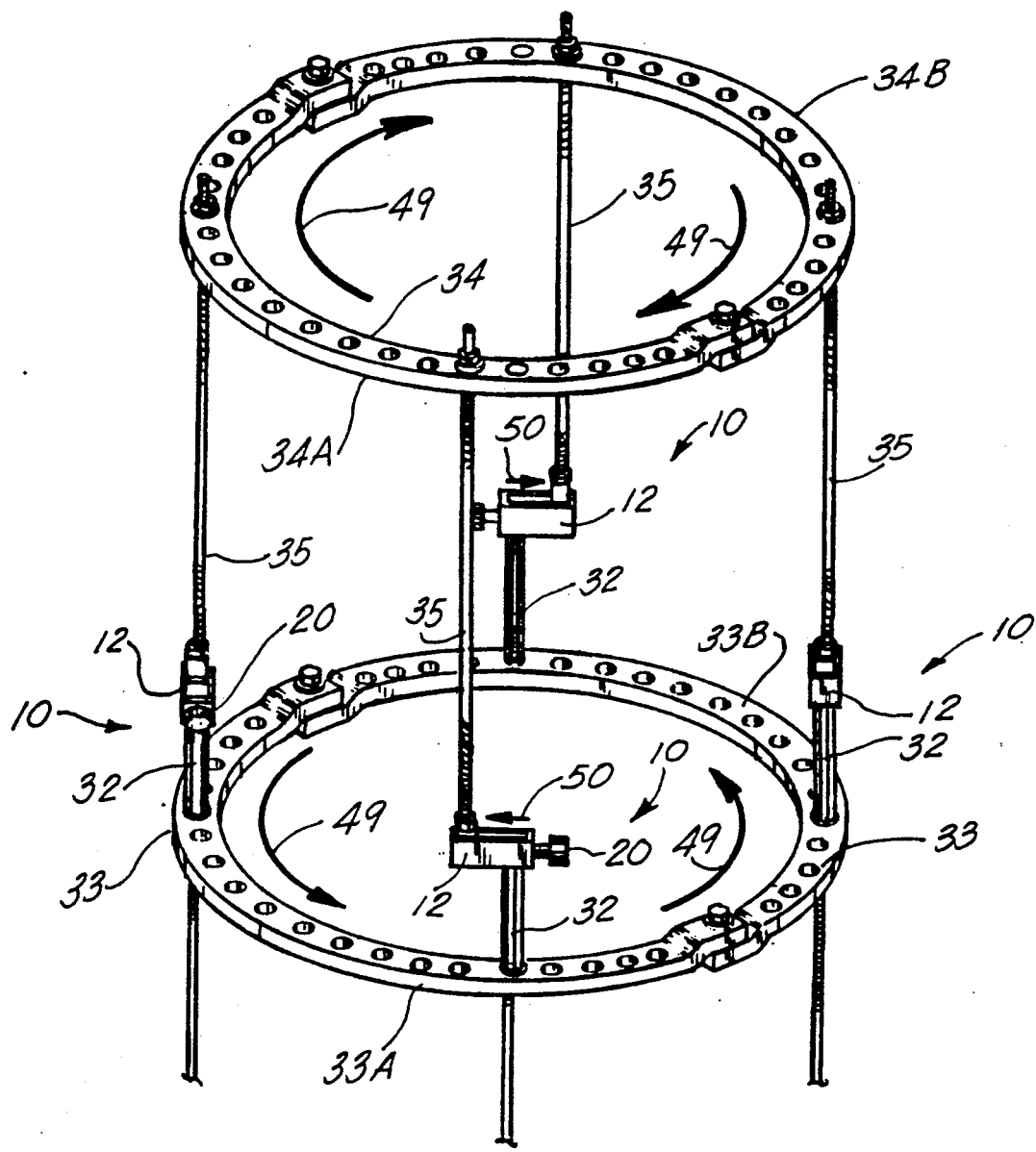
FIG. 3 is a perspective view of the preferred embodiment of the apparatus of the present invention shown in use with a typical "Ilizarov" external fixation system wherein rotational movement of one ring with respect to another ring is illustrated.

FIGS. 1-3 illustrates the preferred embodiment of the apparatus of the present invention designated generally by the numeral 10, used for translation/rotation adjustments of one fixation ring 33 with respect to another ring 34. In FIGS. 1-3 there can be seen apparatus 10 including a base member 12 having a slot 13 surrounded by flat side walls 14, 15 defining the generally rectangular slot 13 there between. End walls 16, 17 are positioned at each end portion of the slot and the slot preferably has an open top 18 and an open bottom 19. The bottom of the slot 19 preferably communicates with a T-shaped longitudinally extending track 19A as shown in FIGS. 1 and 2. The track 19A provides an attachment for the affixation of tie rod 32 to base 12. Tie rod 32 has a similarly shaped, T-shaped upper head portion (not shown) which registers with the T-shaped slot 19A as shown in FIGS. 1 and 3. The connection between tie rod 32 and base 12 is preferably a bolted connection with threaded bolt 35 having a head portion that registers in and fits slot 19A. A cylindrical threaded shank of the bolt passes through a hollow central cylindrical bore of tie rod 32 and through a selected opening 31 of plate 33. A bolted connection 36 then secures the tie rod to ring 33.

Rotatable thumb screw 20 provides a fine adjustment for translation and/or rotation of one ring 33 with respect to another ring 34. Thumb screw 20 includes set screw 21 mounted in opening 23 for connecting thumb screw 20 to end portion 29 of threaded shaft 22 for rotation therewith. Bushing 25 mounts in opening 27 of base member 12. Similarly shaped bushing 24 mounts in similarly shaped opening 26 opposite opening 27 as shown in FIG. 2. Each bushing 24, 25 has an opening 30, 31 respectively through which threaded shaft 22 extends. The end portion 29 of shaft 22 registers with opening 30 of bushing 25, and end portion 28 which inserts through and registers with opening 30 of bushing 24. The end portions 28, 29 define unthreaded end sections of shaft 22. Otherwise, shaft 22 is threaded externally along its length as shown in FIG. 2.

Each ring 33, 34 provides a plurality of radially spaced openings 30 which accommodate tie rods 32, 35. Bolts 36 can be used to attach tie rods 35 to rings 33, 34 as shown in FIGS. 1, 3 and 4–6.

Figure 4:
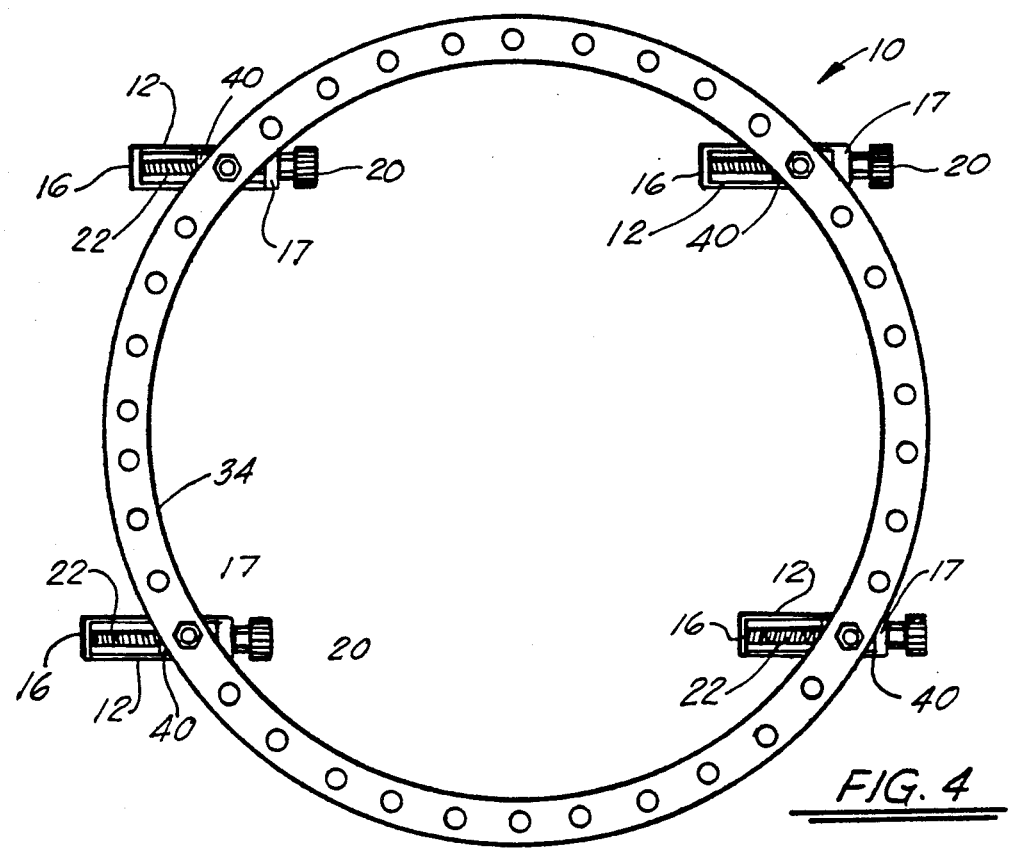
FIG. 4 is a top view of the preferred embodiment of the apparatus of the present invention illustrating two aligned rings prior to translation.
Figure 5:
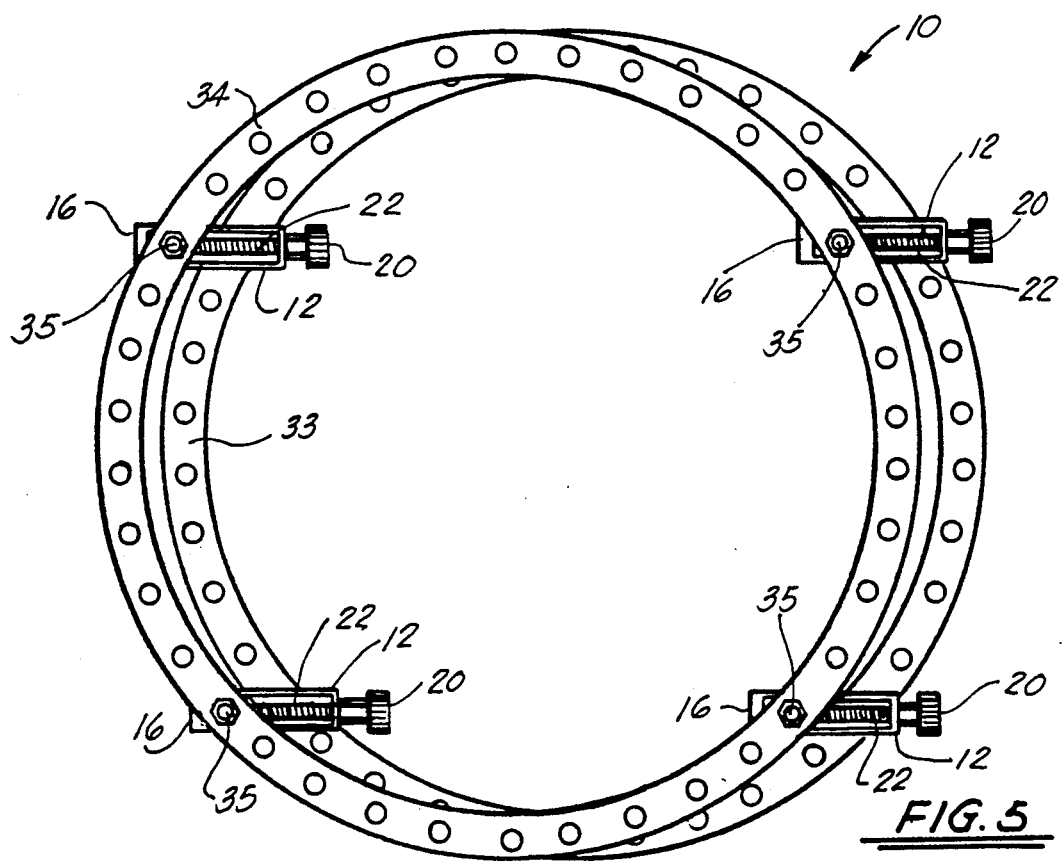
FIG. 5 is another top view of the preferred embodiment of the apparatus of the present invention illustrating a pair of rings after translation has occurred.
Figure 6:
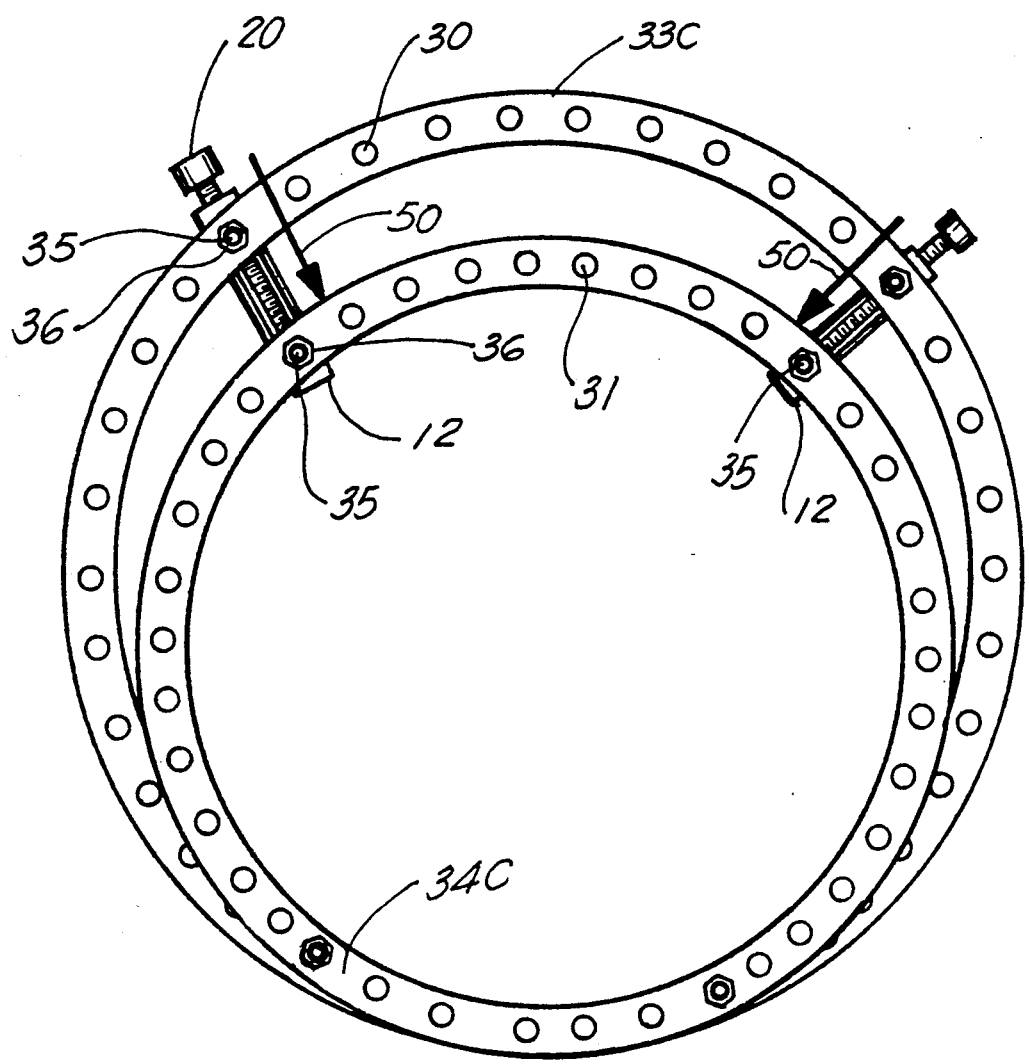
FIG. 6 is another top view of the preferred embodiment of the apparatus of the present invention illustrating translation of a small ring with respect to a larger ring.

Shaft 22 engages translator block 40 at threaded longitudinal bore 47. Thus, rotation of shaft 22 causes translator block 40 to move in slot 13 between end wall 16 and end wall 17. Block 40 is sized to fit in slot 13 as shown in FIG. 1. Block 40 includes end walls 43, 44 and side walls 41, 42 as well as an upper surface 45 having a vertical threaded bore 46 therein. Threaded opening 46 accepts tie rods as shown in FIGS. 1 and 3. In FIG. 1, arrow illustrates the translational movement of block 40 with respect to base 12 and thus the translational movement of tie rod 35 with respect to tie rod 32. FIGS. 4–6 illustrate translation of one ring 33 with respect to another ring 34. The user simply rotates each thumb screw 20 so that the block 40 moves from the first end portion of base 12 at wall 17 to the second end portion of base 12 at wall 16 (FIG. 5). FIG. 5 is a top view showing that the ring members 33, 34 have moved laterally with respect to one another. In FIG. 6, arrows 50 indicate a translational movement of a smaller upper ring 34C with respect to larger lower ring 33C.

In FIG. 3, an arrangement is illustrated for rotation of lower ring 33 with respect to upper ring 34. In the embodiment of FIG. 3, half rings 33A, 33B are shown formed into rings with bolted connections. Curved arrows 49 in FIG. 3 illustrate the rotation and arrows 50 indicate the translational movement of block 40 with respect to base 12. In the embodiment of FIG. 3, the bases are affixed at 90 degrees with respect to one another as shown in the drawing so that the combination of all four traveling blocks 40 with respect to their bases 12 causes a rotation of the ring 34 with respect to the ring 33.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A bone fixator apparatus for the fixation of fractures and the correction of congenital bone deformities, comprising:

(a) upper and lower spaced apart ring-like structures, each having inner and outer annular curved surfaces, and spaced, parallel flat upper and lower surfaces;

(b) a plurality of openings spaced along the ring-like structures, positioned between the inner and outer annular curved surfaces and extending between the upper and lower surfaces;

(c) a plurality of tie rod assemblies including rod members extending during use between the ring-like structures, connecting adjacent ring-like structures together to define a frame and including an upper plurality of tie rods and a lower plurality of tie rods;

(d) fastener means for securing the upper and lower ring-like structures respectively to the upper and lower tie rods, for maintaining spacing between the ring-like structures during use;

(e) translation means interfacing one or more of the upper tie rods and a corresponding one or more of the lower tie rods for moving the upper ring-like structure with respect to the lower ring-like structure along a path transversely with respect to the tie rods, and including a translation body affixed to a first selected one of the upper or lower tie rods;

(f) a traveling block member attachable to a second selected tie rod member, the block movable within the translation body and with respect to the first selected tie rod, and (g) laterally extending means for moving the traveling block with respect to the translation body responsive to a rotation of the laterally extending means.

2. The apparatus of claim 1 wherein the translation means comprises a base with a traveling block portion, and threaded adjustment means for moving the traveling block portion relative to the base, the base and traveling block portions being attachable to first and second of the tie rods.

3. The apparatus of claim 2 wherein the base has a slot therein sized to carry the traveling block.

4. The apparatus of claim 2 wherein the base has opposed openings that accept the threaded adjustment screw.

5. The apparatus of claim 4 wherein the threaded adjustment screw includes a threaded shaft rotatably mounted in the base and traversing the slot.

6. The apparatus of claim 5 further comprising a thumbscrew having a gripping surface thereon for rotating the thumbscrew, and the thumbscrew interfaces with the shaft so that rotation of the thumbscrew rotates the shaft.

7. The apparatus of claim 1 wherein the translation means includes at least two, spaced apart translator structures and there are at least four tie rods connecting the ring-like structures, and two tie rods attach to each of the translator structures.

8. The apparatus of claim 7 wherein each translator structure has a base portion and a traveling block portion movable with respect to the base portion.

9. The apparatus of claim 8 wherein a tie rod affixes to each traveling block portion, and a tie rod attaches to each base portion.

10. A bone fixator apparatus for fixation of fractures and the correction of congenital bone deformities, comprising:

(a) a plurality of upper and lower generally circular rings, each having inner and outer curved surfaces, and generally flat, parallel spaced upper and lower surfaces;

(b) a plurality of circumferentially spaced openings in each ring positioned between the inner and outer curved surfaces and extending between the upper and lower flat surfaces;

(c) a plurality of tie rod assemblies, each including upper and lower corresponding rod members extending between the upper and lower rings and through at least some of the holes in the rings;

(d) fastener mean removably affixable to the rods for maintaining spacing between the rings during use;

(e) fine adjustment means for moving one of the rings with respect to other rings by selective rotation of one ring with respect to the other, lateral movement of one ring with respect to the other or a combination thereof;

(f) the fine adjustment mean including a rotatable member that moves an upper rod member laterally with respect to its corresponding lower rod member in response to rotation of the rotatable member.

* * * * *